United States Patent
Yang (10) Patent No.: US 7,604,824 B2
(45) Date of Patent: Oct. 20, 2009

(54) **METHOD FOR EXTRACTION LECTIN FROM *CHAENOMELES LAGENARIA*, MEDICAL COMPOSITION FOR INHIBITING TUMOR GROWTH, BIOLOGICAL REAGENT FOR DETECTING GLYCOPHORIN A ON BLOOD AND BLOOD TYPING KIT**

(75) Inventor: Kuo-Liang Yang, Hualien (TW)

(73) Assignee: Tzu Chi Buddhist General Hospital, Hualian (TW)

( * ) Notice: Subject to any disclaimer, the term of this patent is extended or adjusted under 35 U.S.C. 154(b) by 617 days.

(21) Appl. No.: 10/924,487

(22) Filed: Aug. 24, 2004

(65) Prior Publication Data

US 2005/0260292 A1   Nov. 24, 2005

(30) Foreign Application Priority Data

May 21, 2004   (TW) ............................... 93114387 A (51) Int. Cl.
   *A61K 36/00*   (2006.01)
(52) U.S. Cl. ..................................... 424/776
(58) Field of Classification Search ..................... None
   See application file for complete search history.

(56) References Cited

U.S. PATENT DOCUMENTS 4,849,510 A * 7/1989 Adachi ..................... 530/395

FOREIGN PATENT DOCUMENTS

| CN | 1040621 A | * | 3/1990 |
| JP | 2001031582 A | * | 2/2001 |

OTHER PUBLICATIONS itmonline   http://www.itmonline.org/articles/chaenomeles/chaenomeles.htm.*
Hasija, Lectin in Agglutination and its Role in Detection of SUgars on the Surface of RBC of Normal and Cancer Patients, 1991, Indian Journal of Clinical Biochemistry, 6, 89-96.*
Nachbar et al., Lectins in the United States diet: a survey of lectins in commonly consumed foods and a review of the literature, 1980, The American Journal of Clinical Nutrition, 33, 2338-2345.*
Ortega-Barria et al., A Toxoplasma Lectin-Like Activity Specific for Sulfated Polysaccharides is Involved in Host Cell Infection, 1999, The Journal of Biological Chemistry, 274, 1267-1276.*
Beham et al., Bateriological and technical testing on an 0.2-micrometer air-eliminating infusion filter, 1981, Anaesthesist, 30, 427-429.*

* cited by examiner

*Primary Examiner*—Michael Meller
*Assistant Examiner*—Catheryne Chen
(74) *Attorney, Agent, or Firm*—Womble Carlyle Sandridge & Rice PLLC (57) ABSTRACT

A *Chaenomeles lagenaria* extract having a lectin specific for glycophorin A and method for extracting the same are proposed. The extract is prepared by homogenizing seeds of *Chaenomeles lagenaria* with a homogenizing agent into a mixture, and the mixture is further processed to produce the extract both effective in inhibiting tumor growth and applicable to a blood typing test.

7 Claims, 6 Drawing Sheets

METHOD FOR EXTRACTION LECTIN FROM *CHAENOMELES LAGENARIA*, MEDICAL COMPOSITION FOR INHIBITING TUMOR GROWTH, BIOLOGICAL REAGENT FOR DETECTING GLYCOPHORIN A ON BLOOD AND BLOOD TYPING KIT

BACKGROUND OF THE INVENTION

1. Field of the Invention

The invention relates to a *Chaenomeles lagenaria* extract and a method for extracting the same, and more particularly, to a *Chaenomeles lagenaria* extract that is effective in tumor growth inhibition and applicable to blood typing and method for extracting the same.

2. Description of the Related Art

The body is made up of many types of cells. Normally, cells grow and divide to produce more cells only when the body needs them. This orderly process helps keep the body healthy. However, some cells may keep dividing when new cells are not needed, these extra cells form a mass of tissue called a tumor. The tumor can be benign or malignant. Benign tumors can often be removed and cells from benign tumors do not spread to other parts of the body, rarely posing a threat to life. Malignant tumors, on the other hand are cancer. Cells in these tumors are abnormal and divide without control or order. They can invade and damage nearby tissues and organs. Also, cancer cells can break away from a malignant tumor and enter the bloodstream or the lymphatic system. As a result, cancer spreads from the original cancer site to form new tumors in other organs. According to statistics announced by the World Health Organization (WHO), more than 10 million people are diagnosed with cancer every year. Cancer causes 6 million deaths every year or 12% of deaths worldwide, and it is even estimated that there will be 15 million new cases every year by 2020.

Unfortunately, current therapies designed for the control and treatment of tumors in general, and malignant tumors in particular, are less than satisfactory. A variety of medical approaches including surgery, chemotherapy and radiotherapy are clearly unfocused and accompanied by unpleasant, and often quite serious, side effects as well as being characterized by limited effectiveness. Other treatment methods based on natural products are currently in use (Lee, K. H., Medical Research Review (1999) 19:569-596) or still in clinical trials (Levya, A., et al., Anticancer Research (2000) 20:1029-1031). These remedies, while they may be effective in particular instances, can hardly be considered to solve the overall problem.

Lectins have been used in a variety of scientific applications. They combine with single monosaccharides, usually in a terminal position in the glycolipid and glycoprotein component of the red cell membrane. Lectins have also been known to combine readily with carbohydrate in studies of erythrocytes, leukocytes, platelets, tissue cells and tumor cells, while some lectins are used as mitogens. Researches have found lectins which plays a role in targeting the tumor cells of certain tissues. In addition, most lectins possess multiple blood group specificities, but a few possess specificity for a single blood group determinant. Some lectins are comprised of a single protein that cross-reacts with two or more red cell surface receptors, whereas others can be separated into fractions, each with different blood group specificity.

Lectins (receptors specific proteins) are proteins present in plants (usually in seeds), invertebrate animals, some of the low vertebrate animals, algae, fungi, and bacteria. However, the role of lectins in living organisms is unclear. Goldstein et al. proposed that lectins are defined by their in vitro biological activities as "sugar-binding proteins or glycoproteins of non-immune origin which agglutinate cells and/or precipitate glycoconjugates". Kocourek et al. suggested that lectins be defined as "sugar-binding proteins or glycoproteins of non-immune origin which are devoid of enzymatic activity towards sugar to which they bind and do not require free glycosidic hydroxyl groups on these sugars for their binding."

*Chaenomeles lagenaria* is a native plant with bright red-orange colored flowers. The plant is also cultivated in Japan, so it is known as Japanese Quince. Since *Chaenomeles lagenaria* is rich in organic acids that inhibit bacteria growth, it has been made into Chinese herbal medicine and used internally and topically to treat pain; especially arthralgia and spasms, but also for skin irritation and swellings. Other researches have found that triperpenoid compounds, such as ursolic acid (UA) and oleanolic acid (OA) isolated and identified in the fruit of *Chaenomeles lagenaria* have shown marked anti-tumor effects on human colon carcinoma cell lines (Li, J., Guo W-J, Yang Q-Y, World Journal of Gastroenterology (2002);8(3):493-495). However, the studies of *Chaenomeles lagenaria* carried out so far have not focused on extracting a lectin or similar substance from *Chaenomeles lagenaria* nor are there any substantial studies relating to therapeutic effects of lectin extracted from *Chaenomeles lagenaria*.

In search of a substance that is both effective in inhibiting tumor growth and applicable to binding to a specific red cell surface receptor, the lectin is extracted from *Chaenomeles lagenaria* to develop a therapeutic agent that meets the above demands with minimum side effects to the animal.

SUMMARY OF THE INVENTION

Therefore, the primary objective of the present invention is to provide a *Chaenomeles lagenaria* extract having a receptor protein specific for glycoprotein A and method for extracting the same, such that the extract is applicable and effective in tumor growth inhibition and blood typing.

Another objective of the present invention is to provide a *Chaenomeles lagenaria* extract having a lectin with a specificity for N-acetyl-D-galactosamine residues of O-glycosidically linked oligosaccharide of the glycophorin A and method for extracting the same.

A further objective of the present invention is to provide a blood typing kit or a biological reagent for detecting glycophorin A on a cell surface and a composition that inhibits tumor growth in mammals with use of the *Chaenomeles lagenaria* extract according to the previous objectives.

In accordance with the above and other objectives, the present invention proposes a *Chaenomeles lagenaria* extract prepared by homogenizing seeds of *Chaenomeles lagenaria* with an appropriate amount of a homogenizing reagent to produce a mixture. The mixture is stored at 4° C. for at least two hours before being subjected to low speed centrifugation at 3000 to 5000 revolutions per minute (rpm) to separate the mixture into pellet and supernatant. The supernatant is collected and filtered through a filter to obtain the extract containing a lectin specific for N-acetyl-D-galactosamine residues of O-glycosidically linked oligosaccharide of the glycophorin A.

The *Chaenomeles lagenaria* extract is prepared according an extraction method of the present invention. The method involves homogenizing seeds of *Chaenomeles lagenaria* with the homogenizing reagent for producing a mixture. The mixture is further processed by storing at 4° C. for at least two hours and then subjecting to low speed centrifugation to separate the mixture into pellet and supernatant. The extract is yielded by collecting and filtering the supernatant through the filter, wherein the extract contains the lectin specific for N-acetyl-D-galactosamine residues of O-glycosidically linked oligosaccharide of the glycophorin A.

According to the present invention, the extract prepared from the seeds of *Chaenomeles lagenaria* is applicable to inhibition of tumor cell growth as observed in an in vivo study using Non Obese Diabetic/Severe Combined Immunodeficient (NOD-SCID) mice previously inoculated with lymphoma, melanoma, and neuroblastoma cell lines respectively. The extract also demonstrates a binding activity specific for a glycoprotein, such as glycophorin A found on the cell surface of the red blood cell. Since the glycophorin A is a constituent of a blood group antigen $En^a$, the extract can be manufactured into a biological reagent that determines the presence or absence of the $En^a$ antigen on the cell surface in a blood typing test.

To provide a further understanding of the invention, the following detailed description illustrates embodiments and examples of the invention, it is to be understood that this detailed description is being provided only for illustration of the invention and not as limiting the scope of this invention.

BRIEF DESCRIPTION OF THE DRAWINGS

The drawings included herein provide a further understanding of the invention. A brief introduction of the drawings is as follows.

Table 1 summarizes the reaction results of hemagglutination tests of the *Chaenomeles lagenaria* extract in the form of *Chaenomeles lagenaria* lectin with untreated RBCs and RBCs pretreated with six different enzymes preparations (Papain-cystein, Papain-EDTA, Trypsin, Bromelain-EDTA, Ficin-EDTA, and Pronase);

Table 2 summarizes the reaction results of hemagglutination tests of absorbed *Chaenomeles lagenaria* lectin with untreated M, MN, and N RBCs;

Table 3 summarizes the reaction results of hemagglutination tests of the *Chaenomeles lagenaria* lectin with the RBCs carrying known antigens sensitive to enzyme treatment;

Table 4 shows results of a hemagglutination test of the *Chaenomeles lagenaria* lectin with the RBCs negative for selected high frequency antigens;

Table 5 shows results of a hemagglutination inhibition test of antisera and lectins by glycophorin A, wherein saline served as an experimental control;

Table 6 shows results of a hemagglutination test of the *Chaenomeles lagenaria* lectin with the RBCs ($M^kN$, $M^gN$, $M^gM^g$, $Mi^v$, En(a−)) having reduced levels of sialic acid; and Table 7 shows results of a hemagglutination inhibition test of the *Chaenomeles lagenaria* lectin against $En^{(a+)}$ cells, wherein 1% of selected sugar or saline (control) was added.

DETAILED DESCRIPTION OF THE EMBODIMENTS

The present invention is described in the following with specific embodiments, so that one skilled in the pertinent art can easily understand other advantages and effects of the present invention from the disclosure of the invention. The present invention is also implemented and applied according to other embodiments, and details are modified based on different views and applications without departing from the spirit of the invention.

The following embodiment only serves to provide exemplary descriptions for the present invention with no intent to limit the scope of the invention.

First Preparation Embodiment (*Chaenomeles lagenaria* Extract)

Figure 1:
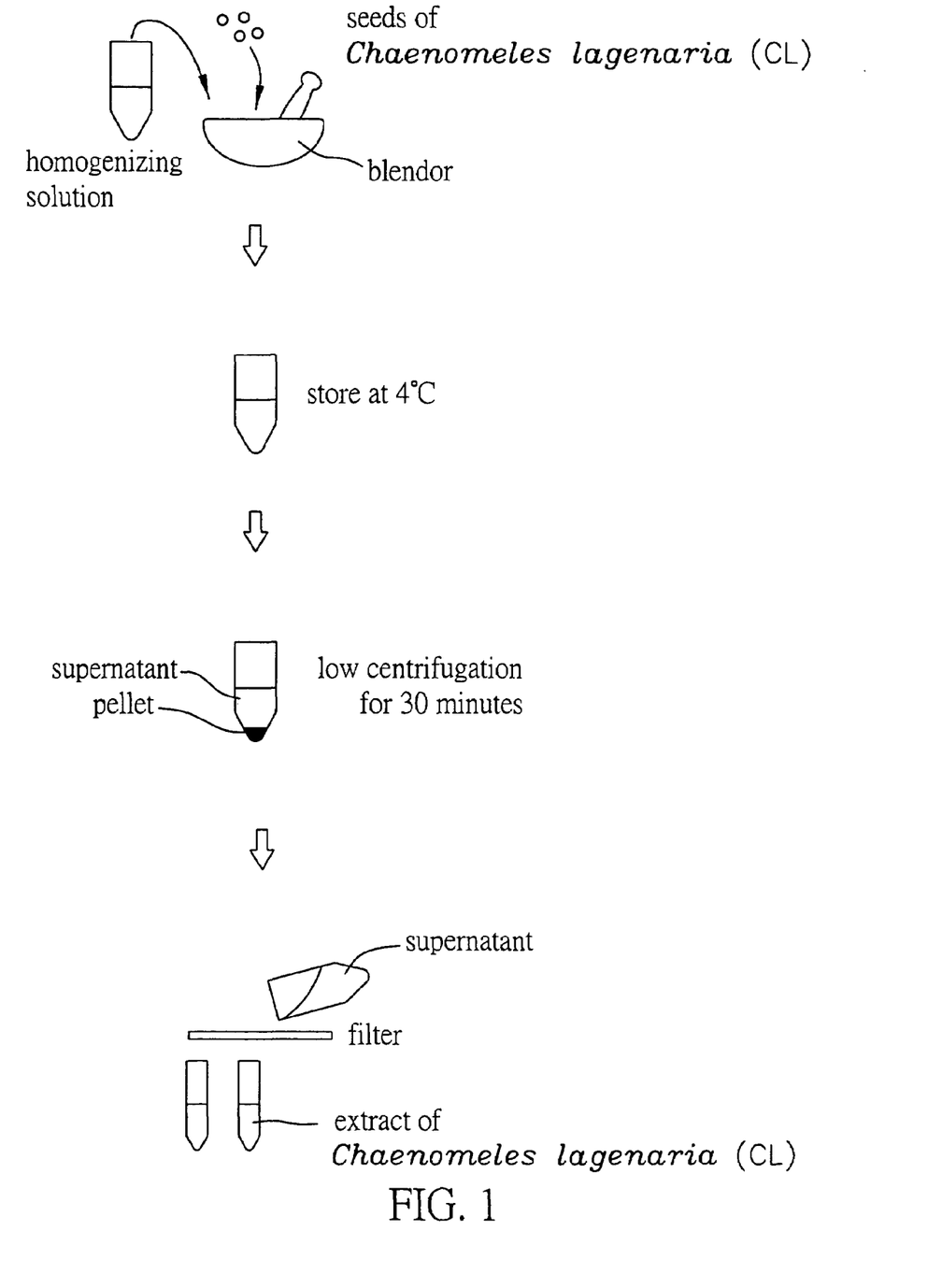
FIG. 1 is a flow chart illustrating a method for extracting a *Chaenomeles lagenaria* extract according to the present invention.

Referring to FIG. 1, the present invention provides a *Chaenomeles lagenaria* extract prepared by homogenizing seeds of *Chaenomeles lagenaria* with an appropriate amount of homogenizing reagent in a ratio of 1:4 in a mixing vessel. In this case, one gram of the seeds is homogenized using 2 ml of phosphate buffered saline (PBS) and 2 ml of glycine reagent in a Waring Blendor to produce a mixture. The mixture is then stored by refrigerating at 4° C. for at least two hours before being subjected to low speed centrifugation, preferably at 5000 revolution per minutes (rpm) for about 30 minutes to separate the mixture into pellet and supernatant. The supernatant is collected and filtered through a Cuno™ filter to obtain a liquid extract. The liquid extract is then dispensed into aliquots and further stored at 4° C. to keep the extract biologically stable. The extract may contain a receptor specific protein specific for glycophorin A, and more preferably the extract contains a lectin specific for N-acetyl-D-galactosamine residues of β-glycosidically linked oligosaccharide of the glycophorin A.

Second Preparation Embodiment (*Chaenomeles lagenaria* Extract)

Alternatively, the extract for studies on the effect of tumor inhibitory activity is prepared by homogenizing one gram of the seeds with 4 ml of saline in a blender. The mixture is refrigerated at 4° C. overnight before centrifugation at 3000 rpm for 30 minutes to separate the mixture into pellet and supernatant. The supernatant is collected and filtered through a 0.2 µM Millipore filter to obtain a liquid extract. The liquid extract obtained is dispensed into aliquots and stored at 4° C. until use. Similarly, the extract may contain a receptor specific protein specific for glycophorin A, and more preferably the extract may contain a lectin specific for N-acetyl-D-galactosamine residues of O-glycosidically linked oligosaccharide of the glycophorin A.

Third Preparation Embodiment (Preparation of Red Blood Cells (RBCs))

RBCs of all ABO groups were obtained from donations collected in citrate phosphate dextrose (CPD). The RBCs were washed at least three times with PBS and 3-5% of the RBCs suspended in PBS were used.

T-activated RBCs were prepared by adding 0.4 ml of neuroaminidase solution to 0.1 ml of the RBCs, and a mixture thereof was incubated at 22° C. for 30 minutes. After incubation, the RBCs were washed four times with PBS and suspended in PBS to produce a 5% suspension. T-activated RBCs were tested with anti-T lectin to ensure the action of neuroaminidase.

Fourth Preparation Embodiment (Glycophorin A)

Glycophorin A was prepared using a butanol extraction procedure. First of all, 20 ml of group 0 MN RBCs in CPD were washed twice with 50 ml of 0.103 mol/L $Na_2HPO_4$ and lysed by a lysis buffer. The lysed cells were subjected to centrifugation at 12,000 rpm for 30 minutes and washed once with the same buffer to yield readily dispersed pale yellowish-pink "ghost" or empty shells of the RBCs in a pellet form. The pellet was made up to 5.5 ml with the same buffer to which 11 ml of ice-cold n-butanol was added. The mixture was vigorously shaken for 20 seconds and then kept on ice for 15 minutes. The aqueous phase was carefully removed and dialyzed overnight at 4° C. against two exchanges of 0.1 mmol/L sodium phosphate buffer, pH 7.0 to yield a solution. The solution was then concentrated by pressure dialysis under nitrogen gas over an Amicon™ UM10 membrane to 2 ml.

EXPERIMENTAL EXAMPLES

Tumor Growth Inhibition (In Vivo):

Each of the selected tumor cells, including lymphoma cells (of Raji and P3HR-1 cell line), neuroblastoma cells (of SKN-AS cell line), and melanoma cells (of Bowes cell line) were suspended in the normal saline or an equal amount of the *Chaenomeles lagenaria* extract prepared according to the first and second preparation embodiment. Preferably, the lymphoma cells at a concentration of $7 \times 10^4$ were suspended in 1 mL of 0.9% normal saline or 1 mL of the *Chaenomeles lagenaria* extract, the neuroblastoma cells at a concentration of $3 \times 10^5$ were suspended in 1 mL of 0.9% normal saline or 1 mL of the *Chaenomeles lagenaria* extract, and the melanoma cells at a concentration of $2.2 \times 10^4$ were suspended in 0.4 mL of 0.9% normal saline or 0.4 mL of the *Chaenomeles lagenaria* extract.

The tumor cell suspension (1 mL of the lymphoma cells or 1 mL of the neuroblastoma cells or 0.4 mL of the melanoma cells) in either the normal saline or the *Chaenomeles lagenaria* extract was then injected into the abdomens of 4-5 week old Non Obese Diabetic/Severe Combined Immunodeficient (NOD-SCID) mice. In this case, the tumor cell suspension in the normal saline was injected subcutaneously on one side of the abdomen, and the same amount of the tumor cell suspension in the *Chaenomeles lagenaria* extract was injected by the same manner on the opposite side of the abdomen.

Figure 2:
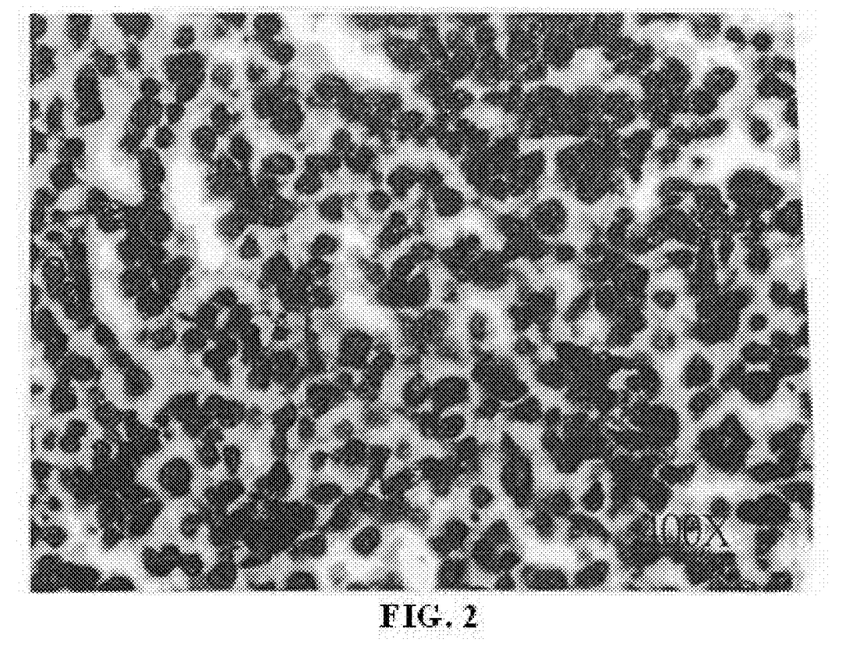
FIG. 2 is a photographic image (magnified by 400 times) illustrating lymphoma cells (Raji or P3HR-1) in a tissue dissected from a tumor formed as a result of injecting the lymphoma cells suspended in phosphate buffer saline (PBS) into the abdomen of a Non Obese Diabetic/Severe Combined Immunodeficient (NOD-SCID) mouse.
Figure 3:
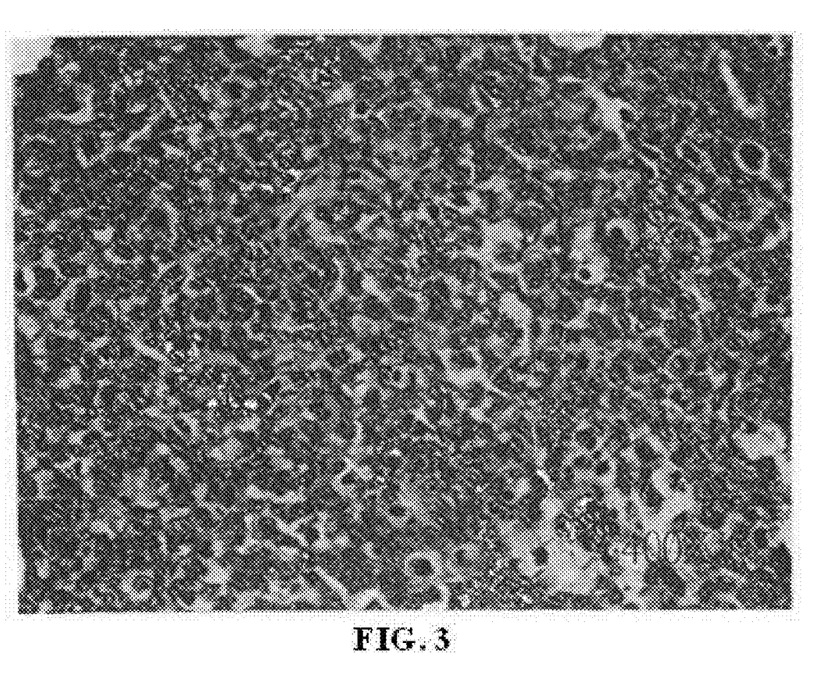
FIG. 3 is a photographic image (magnified by 400 times) illustrating neuroblastoma cells (SKN-AS) in a tissue dissected from a tumor formed as a result of injecting the neuroblastoma cells suspended in PBS into abdomen of the NOD-SCID mouse.
Figure 4:
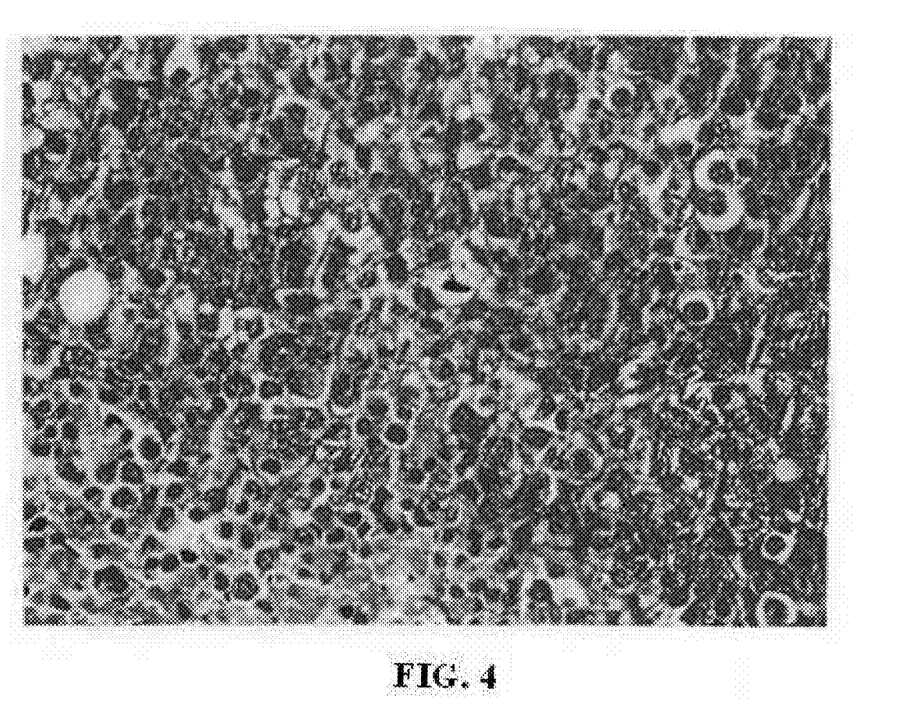
FIG. 4 is a photographic image (magnified by 400 times) illustrating melanoma cells (Bowes) in a tissue dissected from a tumor formed as a result of injecting the melanoma cells suspended in PBS into the abdomen of a NOD-SCID mouse.

After the tumor cells were injected into the mice for a period of 4-5 weeks, the mice were examined progressively for any tumor formation on both sides of the abdomen. Tumor formation was confirmed by dissecting the abdomen for which tumor cells suspended in either saline or the *Chaenomeles lagenaria* extract had been injected. The tumor tissues were collected and stored in a 30% formaldehyde solution prior to pathological investigation under microscope. Tumor formations and lymphoma, neuroblastoma, and melanoma cells were observed by staining the tumor tissues as illustrated in FIGS. 2 through to 4, respectively. Since tissue staining is a well-known technique and involves different approaches, the details thereof are omitted herein.

After an incubation period of 4-5 weeks, tumors that resulted from an irregular growth of lymphoma cells (Raji and P3HR-1) were observed on the side of the abdomen injected with the lymphoma cells suspended in saline solution, indicating that lymphoma cells suspended in saline solution were allowed to grow into tumors. The tumors were further analyzed for their cellular morphology with reference to FIG. 2. On the other hand, the lymphoma cells suspended in the *Chaenomeles lagenaria* extract clearly did not invoke tumor growth as there was no swelling found on the opposite side of the abdomen (not shown).

Also, the tumors that resulted from an irregular growth of neuroblastoma cells (SKN-AS) were observed on the side of the abdomen injected with the neuroblastoma cells suspended in saline solution, indicating that the neuroblastoma cells suspended in saline solution were allowed to grow into tumors. The tumors were further analyzed for their cellular morphology with reference to FIG. 3. On the other hand, the neuroblastoma cells suspended in the *Chaenomeles lagenaria* extract clearly did not invoke tumor growth as there was no swelling found on the opposite side of the abdomen (not shown).

Furthermore, the tumors that resulted from an irregular growth of melanoma cells (Bowes) were observed on the side of the abdomen injected with the melanoma cells suspended in saline solution, indicating that the melanoma cells suspended in PBS were allowed to grow into tumors. The tumors were further analyzed for their cellular morphology with reference to FIG. 4. On the other hand, the melanoma cells suspended in the *Chaenomeles lagenaria* extract clearly did not invoke tumor growth as there was no swelling found on the opposite side of the abdomen (not shown).

Tumor Growth Inhibition (In Vitro):

The tumor cell suspension (1 mL of the lymphoma cells (of Raji and P3HR-1 cell line) or 1 mL of the neuroblastoma cells) in either the normal saline or the *Chaenomeles lagenaria* extract was cultured and supplemented with an appropriate cell culture medium, such as Dulbecco's Modified Eagle Medium (DMEM) in a cell culture vessel. The cell culture was maintained in a cell culture incubator (37° C., 5% $CO_2$) and observed under phase contract microscopy. Since the cell culture technique is well known to one skilled in the art, the details are omitted herein.

The number and viability of the tumor cells suspended in PBS or the *Chaenomeles lagenaria* extract were determined and followed for several consecutive days in FIGS. 5A, 5B, 6A, 6B, 7A and 7B, respectively. The cell numbers were counted by using a hematocytometer.

Figure 5A:
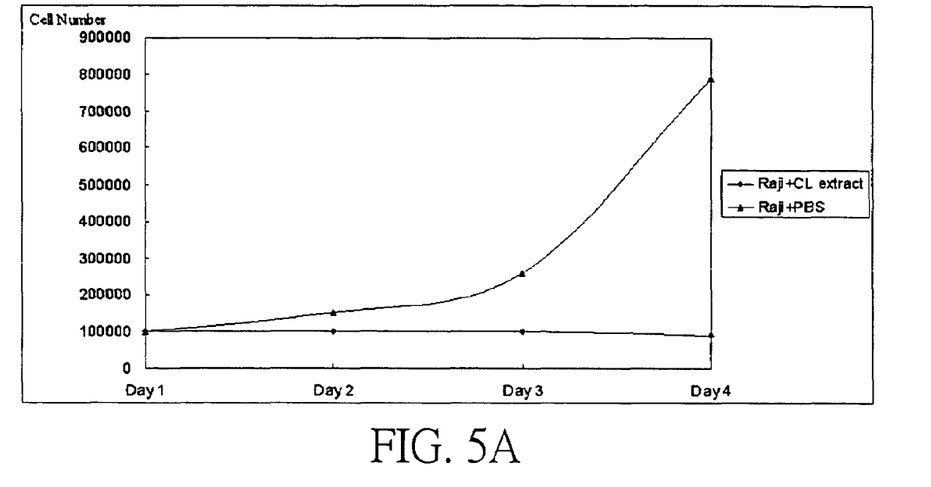
FIG. 5A illustrates changes of lymphoma cell number with respect to time (number of days) after the lymphoma cells (Raji) suspended in either PBS or *Chaenomeles lagenaria* (CL) extract were cultured in petridishes, and FIG. 5B progressively illustrates lymphoma cell viability calculated as a percentage of the surviving lymphoma cells of the total lymphoma cells suspended in either PBS or CL extract after a proliferation period.
Figure 5B:
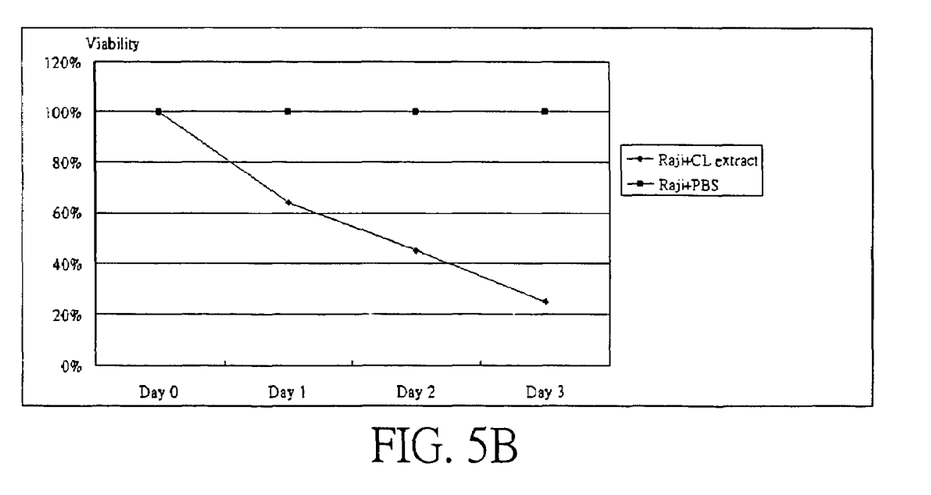
Figure 6A:
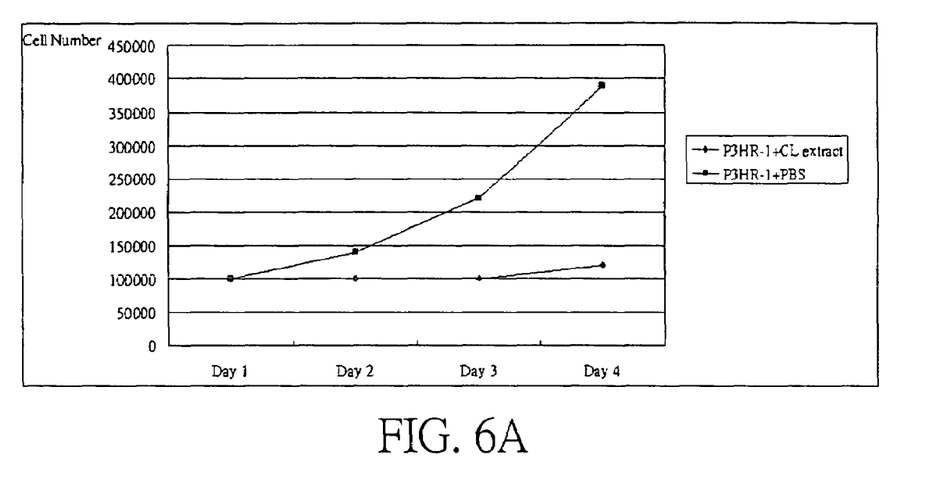
FIG. 6A illustrates changes of lymphoma cell number with respect to time (number of days) after the lymphoma cells (P3HR-1) suspended in either PBS or CL extract were cultured in petridishes, and FIG. 6B progressively illustrates lymphoma cell viability calculated as a percentage of the surviving lymphoma cells of the total lymphoma cells suspended in either PBS or CL extract after a proliferation period.
Figure 6B:
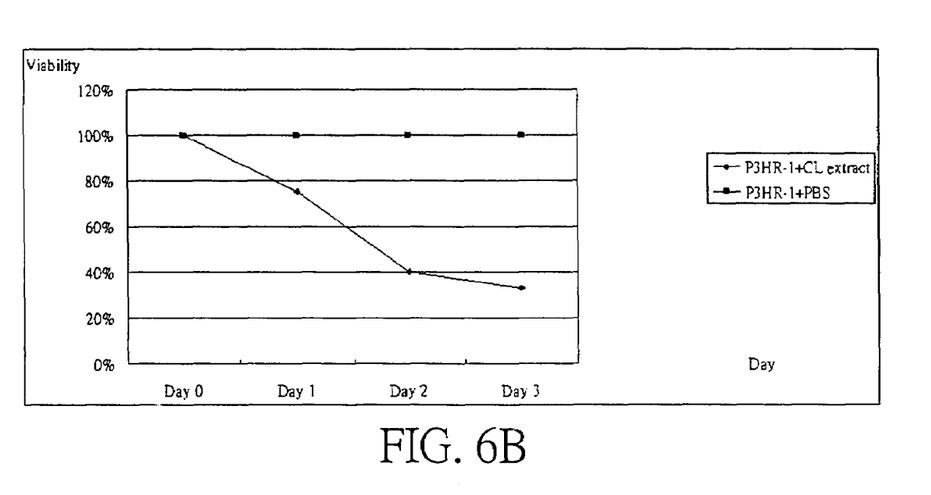

More tumorgenic effect of the lymphoma cells could also be evident in FIGS. 5A and 6A both showing a gradual increase of cell numbers from Day 1, followed by a much sharper increase from Day 3 to Day 4 after the lymphoma cells suspended in PBS were cultured in a petridish. By comparison, the lymphoma cells suspended in the *Chaenomeles lagenaria* (CL) extract did not change significantly in number. Referring to FIGS. 5B and 6B, the lymphoma cells suspended in PBS remained 100% viable throughout a period of 3 days. However, the lymphoma cells suspended in the CL extract constantly lost their viability, decreasing from 100% at the beginning to about 20-30% at the end over a 3 day period. Therefore, it is apparent that the CL extract inhibited in this case the tumor growth in terms of degrading lymphoma cell viability.

Figure 7A:
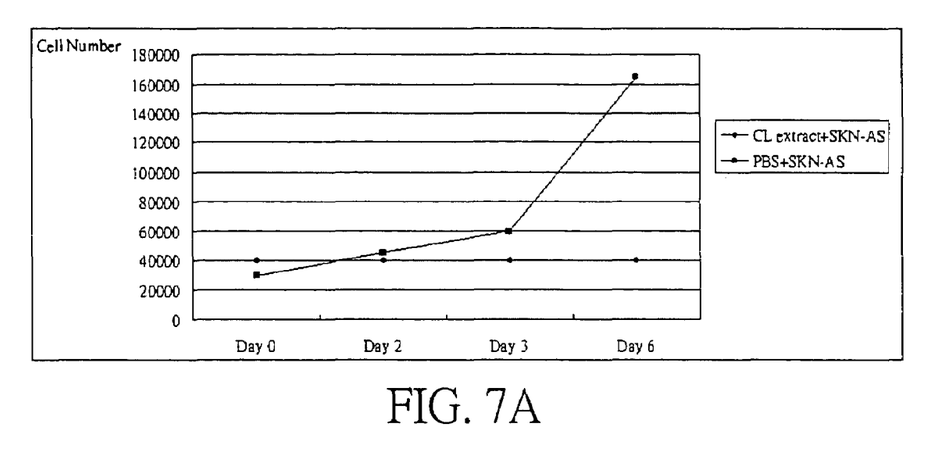
FIG. 7A illustrates changes of lymphoma cell number with respect to time (number of days) after the neuroblastoma cells (SKN-AS) suspended in either PBS or CL extract were cultured in petridishes, and FIG. 7B progressively illustrates neuroblastoma cell viability calculated as a percentage of the surviving neuroblastoma cells of the total neuroblastoma cells suspended in either PBS or CL extract after a proliferation period.
Figure 7B:
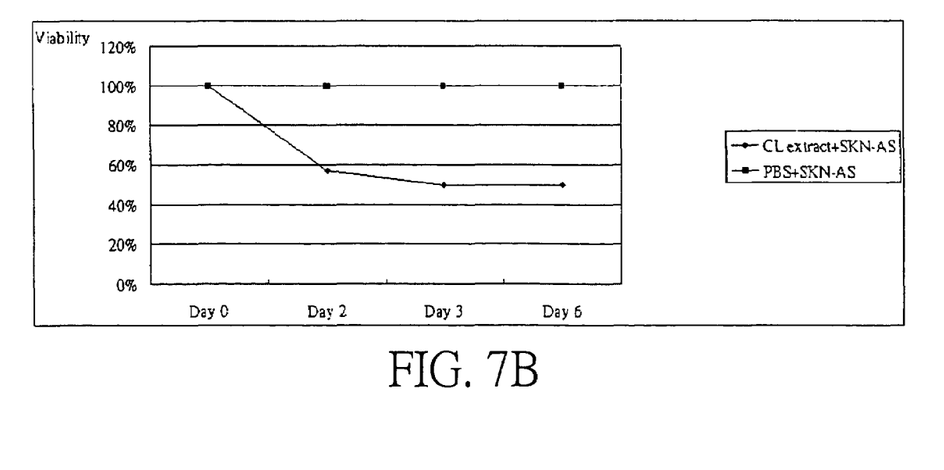

Similarly, as is evident in FIG. 7A, a gradual increase of the neuroblastoma cells was seen beginning from Day 1, followed by a much sharper increase from Day 3 to Day 6 after the neuroblastoma cells suspended in PBS were cultured in a petridish. By comparison, the neuroblastoma cells suspended in the CL extract did not change significantly in number. Referring to FIG. 7B, the neuroblastoma cells suspended in PBS remained 100% viable throughout a period of 6 days. However, the lymphoma cells suspended in the CL extract constantly lost their viability, decreasing from 100% at the beginning to about 50% at the end over a 6 day period. Therefore, it is apparent that the CL extract inhibited in this case the tumor growth in terms of degrading neuroblastoma cell viability.

Blood Typing Test:

(a) Hemagglutination Test:

A hemagglutination test was performed by mixing two drops of the *Chaenomeles lagenaria* extract prepared according to the first or second preparation embodiment with each drop of the RBC suspension prepared according to the third preparation embodiment in a 10×75 mm culture tube. The tube was subjected to low-speed centrifugation at 3400 rpm for at least 15 seconds before the result was examined macroscopically and microscopically for agglutination and hemolysis. An agglutination reaction is evident by a positive sign, whereas a negative sign indicates hemolysis or no agglutination reaction.

(b) Hemagglutination Inhibition Test:

A hemagglutination inhibition test was carried out by mixing equal volumes of the *Chaenomeles lagenaria* extract and the test substance including selected sugars (N-acetyl-D-galactosamine, D(+) galactose, L(−) fucose, d(+) mannose, D-glucose, N-acetylneuraminic acid, N-acetyl-D-glucosamine), glycophorin A, and saline, before incubating the mixture at 22° C. for 30 minutes. For every two drops of the above mixture, one drop of the RBC suspension was added as an indicator. Then, the mixture was centrifuged at 3400 rpm for at least 15 seconds before the result was examined macroscopically and microscopically for agglutination and hemolysis. An agglutination reaction is evident by a positive sign, whereas a negative sign indicates no agglutination reaction.

(c) Absorption Assay:

In the absorption assay, equal volumes of the RBC suspension and the *Chaenomeles lagenaria* extract were mixed and incubated at 22° C. for 30 minutes. The absorbed extract was collected after centrifugation at 3400 rpm for five minutes and stored at 4° C. before use.

As evident to results in Table 1, the *Chaenomeles lagenaria* extract agglutinated the untreated RBCs as shown by positive signs but failed to agglutinate the RBCs pretreated with any of the selected enzymes (Papain-cystein, Papain-EDTA, Trypsin, Bromelain-EDTA, Ficin-EDTA, and Pronase) as indicated by negative signs. The table of results demonstrates that the *Chaenomeles lagenaria* extract in the form of *Chaenomeles lagenaria* lectin detects receptors situated in the protease-labile portion of the RBCs membrane. In order to verify that the *Chaenomeles lagenaria* lectin indeed detects the receptors present in untreated but not in proteolytic enzyme pretreated RBCs, the lectin was absorbed by untreated and papain-cystein pretreated RBCs in a manner described in the absorption assay. The absorbed lectin was then tested with untreated RBCs carried with M, N, and MN antigens respectively. From Table 2, it shows that the untreated RBCs removed the agglutination activity of the extract whereas enzyme pretreated RBCs did not, confirming that receptors for the *Chaenomeles lagenaria* lectin are located in the protease-labile portion of the RBCs membrane.

Since the *Chaenomeles lagenaria* lectin did not react with the RBCs pretreated with various proteolytic enzymes, the RBCs carried with antigens (such as M, N, S, s, U, $Fy^a$ $Fy^b$, and $Fy^3$) known to be sensitive to enzyme digestion were tested with the extract. Results in Table 3 suggests the *Chaenomeles lagenaria* lectin is not specific for the antigens above, since all the RBCs pretreated with papain-cystein show no hemagglutination reaction with the *Chaenomeles lagenaria* lectin, while the RBCs with no enzyme treatment all show positive hemagglutination reaction with the *Chaenomeles lagenaria* lectin. Further evidence from Table 4 indicates that the specificity of the *Chaenomeles lagenaria* lectin is $En^a$ antigen, since all of the RBCs tested except those RBCs ($En^{(a-)}$ cells) lacking $En^a$ antigen show positive reaction with the *Chaenomeles lagenaria* lectin in the hemagglutination test.

The $En^{(a-)}$ cells are known to behave exactly like proteolytic enzyme pretreated cells that have a 40% to 50% reduction in sialic acid content and are totally deficient of erythrocyte membrane MN sialoglycoprotein (glycophorin A). Glycophorin A is known to carry M, N, or $En^a$ antigen. Inhibition of human anti-$En^a$ by glycophorin A has been reported. Table 5 shows results of a hemagglutination inhibition test of selected antisera and *Chaenomeles lagenaria* lectin against the RBCs by glycophorin A. Glycophorin A was found to inhibit anti-M, anti-N, human anti-$En^a$ and anti-$En^a$ lectin of *Chaenomeles lagenaria* as indicated by the negative signs in Table 5, while saline solutions did not inhibit hemagglutination reaction with RBCs. This result confirms that the specificity of *Chaenomeles lagenaria* lectin is anti-$En^a$. It has also been found that $M^k$, $M^g$ and $Mi^v$ cells have reduced levels of sialic acid. Therefore, the *Chaenomeles lagenaria* lectin was tested with these cells to determine whether the lectin contains specificity associated with reduced levels of sialic acid. Results shown in Table 6 exclude the anti-$En^a$ specificity of the *Chaenomeles lagenaria* lectin being associated with other antigens ($M^k$, $M^g$ and $Mi^v$) found on the RBCs with reduced levels of sialic acid.

Next, a hemagglutination inhibition test of the *Chaenomeles lagenaria* lectin against $En^{(a+)}$ cells was conducted using 1% simple sugar solutions (N-acetyl-D-galactosamine, D(+) galactose, L(−) fucose, d(+) mannose, D-glucose, N-acetylneuraminic acid, N-acetyl-D-glucosamine). As shown in Table 7, the positive reaction with the *Chaenomeles lagenaria* lectin was observed using D(+) galactose, L(−) fucose, d(+) mannose, D-glucose, N-acetyl-D-glucosamine, and N-acetylneuroaminic acid, but it was found that N-acetyl-D-galactosamine completely inhibit the activity of the extract against the En$^{(a+)}$ cells. This suggests that the lectin of the *Chaenomeles lagenaria* is specific for the N-acetyl-D-galactosamine residues of O-glycosidically linked oligosaccharide of the glycophorin A.

Summarizing from the above, it is understood that the extract prepared from the seeds of *Chaenomeles lagenaria* in the form of the *Chaenomeles lagenaria* lectin according to the present invention is effective in inhibiting tumor cell growth as observed in an in vivo study using NOD-SCID mice inoculated with lymphoma, melanoma, and neuroblastoma cell lines respectively. Thus, the *Chaenomeles lagenaria* lectin may be used in making a composition that effectively inhibit growth of the tumor. The extract also demonstrates a binding activity specific for a glycoprotein, such as glycophorin A found on the cell surface of red blood cells. Since the glycophorin A is a constituent of a blood group antigen En$^a$, the extract can be manufactured into a biological reagent or kit that determines the presence or absence of the En$^a$ antigen on the cell surface in the blood typing test.

It should be apparent to those skilled in the art that the above description is only illustrative of specific embodiments and examples of the invention. The invention should therefore cover various modifications and variations made to the herein-described structure and operations of the invention, provided they fall within the scope of the invention as defined in the following appended claims.

TABLE 1

Hemagglutination test of *Chaenomeles lagenaria* lectin with pretreated red cells

| Red cells pretreated with | Reaction |
|---|---|
| Saline | +++ |
| Papain-cystein | − |
| Papain-EDTA | − |
| Trypsin | − |
| Bromelain-EDTA | − |
| Ficin-EDTA | − |
| Pronase | − |

TABLE 2

Hemagglutination test of absorbed *Chaenomeles lagenaria* lectin with red cells

| | Reaction with test cells | | |
|---|---|---|---|
| Extract | M | MN | N |
| Absorbed by untreated cells | − | − | − |
| Absorbed by papain-cystem Pretreated cells | +++ | +++ | +++ |
| Unabsorbed | +++ | +++ | +++ |

TABLE 3

Hemagglutination test of *Chaenomeles lagenaria* lectin with red cells carry antigen known sensitive to enzyme treatment

| | Reaction | |
|---|---|---|
| Red cells | No treatment | After treatment* |
| M | +++ | − |
| MN | +++ | − |

TABLE 3-continued

Hemagglutination test of *Chaenomeles lagenaria* lectin with red cells carry antigen known sensitive to enzyme treatment

| | Reaction | |
|---|---|---|
| Red cells | No treatment | After treatment* |
| N | +++ | − |
| S | +++ | − |
| Ss | +++ | − |
| s | +++ | − |
| U(−) | +++ | − |
| Fy(a+b−) | +++ | − |
| Fy(a−b+) | +++ | − |
| Fy:3 | +++ | − |

*By papain-cystein

TABLE 4

Hemagglutination test of *Chaenomeles lagenaria* lectin with red cells negative for certain high frequency antigens

| Red cells | Reaction | Red cells | Reaction |
|---|---|---|---|
| En(a−) | − | At(a−) | +++ |
| En(a−) | − | I− | +++ |
| Tj(a−) | +++ | Lu(b−) | +++ |
| Co(a−) | +++ | K$_o$ | +++ |
| Wr(b−) | +++ | Di(b−) | +++ |
| Cr(a−) | +++ | Gy(a−) | +++ |
| Jo(a−) | +++ | Hy− | +++ |
| Do(a−) | +++ | Rg(a−) | +++ |
| Vel− | +++ | Tc(a−) | +++ |
| Ge− | +++ | Cs(a−) | +++ |
| Lan− | +++ | Kp(b−) | +++ |
| Yk(a−) | +++ | U− | +++ |
| Jr(a−) | +++ | Jk−3 | +++ |
| Sd(a−) | +++ | Au(a−) | +++ |
| Rh$_{null}$ | +++ | McC(a−) | +++ |
| O$_h$ | +++ | Kn(a−) | +++ |
| JMH | +++ | Lw− | +++ |

TABLE 5

Hemagglutination inhibition test of antisera and lectins by glycophorin A

| | Hemagglutination inhibition Substance | |
|---|---|---|
| Antisera/lectins | Glycophorin A | Saline |
| *C. lagenaria* | − | +++ |
| Anti-En$^a$ | − | ++++ |
| Anti-M | − | ++ |
| Anti-N | − | ++ |
| Anti-D | +++ | +++ |
| Anti-k | +++ | +++ |
| Anti-Lu$^b$ | + | + |
| Anti-U | ++ | ++ |
| Anti-T lectin | ++++ | ++++ |

TABLE 6

Hemagglutination test of *Choenomeles lagenaria* lectin with red cells which have reduced levels of sialic acid

| Cells | Hemagglutination |
|---|---|
| M$^k$N | +++ |
| M$^g$N | +++ |

TABLE 6-continued

Hemagglutination test of *Choenomeles lagenaria* lectin with red cells which have reduced levels of sialic acid

| Cells | Hemagglutination |
|---|---|
| $M^gM^g$ | +++ |
| $Mi^v$ | +++ |
| En(a−) | − |

TABLE

Hemagglutination inhibition test of *Chaenomeles lagenaria* lectin against En(a+) cells

| Sugar (1%) | Hemagglutination inhibition |
|---|---|
| N-acetyl-D-galactosamine | − |
| D(+) galactose | +++ |
| L(−) fucose | +++ |
| d(+) mannose | +++ |
| D-glucose | +++ |
| N-acetylneuraminic acid | +++ |
| N-acetyl-D-glucosamine | +++ |
| Saline control | +++ |

What is claimed is:

1. A method for extracting a *Chaenomeles lagenaria* extract containing lectin specific for N-acetyl-D-galactosamine residues of O-glycosidically linked oligosaccharide of glycophorin A, comprising the steps of: homogenizing *Chaenomeles lagenaria* seeds with a homogenizing agent comprising phosphate buffered saline and glycine to produce a mixture; subjecting the mixture to centrifugation to separate the mixture into a pellet and supernatant; and collecting and filtering the supernatant to obtain the *Chaenomeles lagenaria* extract.

2. The method of claim 1, wherein the mixture is stored at 4° C. for at least two hours before subjecting to centrifugation.

3. The method of claim 1, wherein in the homogenizing step, 1 g of the *Chaenomeles lagenaria* seeds are homogenized with 4 ml of the homogenizing agent to produce the mixture.

4. The method of claim 1, wherein a volume ratio of phosphate buffered saline and glycine in the homogenizing agent is 1:1.

5. The method of claim 1, wherein the mixture is subjected to centrifugation at 3000 to 5000 revolutions per minute (rpm).

6. The method of claim 5, wherein the mixture is subjected to centrifugation for at least 30 minutes.

7. The method of claim 1, wherein the supernatant is filtered through a filter having a pore size of 0.2 μm.

* * * * *